United States Patent [19]

Varma et al.

[11] Patent Number: 5,049,578
[45] Date of Patent: Sep. 17, 1991

[54] 1-AROYL OR 1-ACYL-2-2PYRROLIDINYL-3,5-DIHYDROXY ALKANOIC AND ALKENOIC ACIDS, SALTS, ESTERS AND LACTONES

[75] Inventors: Ravi K. Varma, Belle Mead; Eric M. Gordon, Pennington, both of N.J.

[73] Assignee: E. R. Squibb & Sons, Inc., Princeton, N.J.

[21] Appl. No.: 490,901

[22] Filed: Mar. 9, 1990

[51] Int. Cl.$^5$ .................. A61K 31/40; C07D 207/08; C07D 405/06
[52] U.S. Cl. ............................. 514/409; 514/422; 514/423; 548/408; 548/517; 548/539; 548/540
[58] Field of Search ............... 548/408, 539, 540, 517; 514/409, 423, 422

[56] References Cited

U.S. PATENT DOCUMENTS

| | | | |
|---|---|---|---|
| 3,975,399 | 8/1976 | De Franco et al. | 260/326.2 |
| 4,452,807 | 6/1984 | Aschwanden et al. | 424/274 |
| 4,461,906 | 7/1984 | Aschwanden et al. | 548/406 |
| 4,515,960 | 5/1985 | Teetz | 548/408 |
| 4,731,456 | 3/1988 | Hartwig | 548/539 |
| 4,800,212 | 1/1989 | Evans et al. | 514/424 |
| 4,929,633 | 5/1990 | Shibahara et al. | 548/540 |

FOREIGN PATENT DOCUMENTS 0221025 5/1987 European Pat. Off.
WO8607054 12/1986 PCT Int'l Appl.

OTHER PUBLICATIONS

Mauger, A. B., J. Org. Chem., 46 (1982), pp. 1032-1035.
Cocolas, G. H. et al., J. Am. Chem. Soc. 79 (1957), pp. 5203-5205.
Delaney, N. G. et al., J. Am. Chem. Soc. 104 (1982), pp. 6635-6641.
Hartwig, W. et al., J. Org. Chem., 52 (1987), pp. 4352-4358.

Primary Examiner—Joseph P. Brust
Attorney, Agent, or Firm—Timothy J. Gaul

[57] ABSTRACT

Antihypercholesterolemic activity is exhibited by novel compounds of the formula

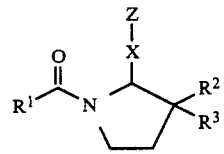

wherein:
Z is

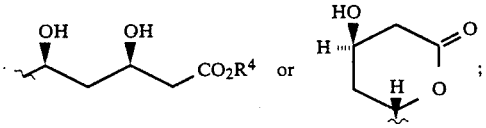

X is lower alkyl or lower alenyl;
$R^1$ is aryl or alkyl;
$R^2$ and $R^3$ are the same or different and are hydrogen, or lower alkyl or aryl, or $R^2$ and $R^3$ taken together to form a cycloalkyl group; and
$R^4$ is hydrogen, lower alkyl, or alkali metal (such as sodium, lithium, or potassium) or a radical such as ammonium.

Methods of use and novel intermediates of these compounds are also provided.

10 Claims, No Drawings

1-AROYL OR 1-ACYL-2-2PYRROLIDINYL-3,5-DIHYDROXY ALKANOIC AND ALKENOIC ACIDS, SALTS, ESTERS AND LACTONES

FIELD OF THE INVENTION

The present invention relates to 1-aroyl or 1-acyl-2-pyrrolidinyl-3,5-dihydroxy alkanoic and alkenoic acids, salts, esters and lactones, which are HMG-CoA reductase inhibitors useful as anti-hypercholesterolemic agents, and to methods of use and intermediates for preparing such compounds.

DESCRIPTION OF THE INVENTION

In accordance with the present invention, compounds having the structure

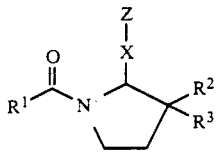

and pharmaceutically acceptable salts thereof have been found to possess activity as HMG-CoA reductase inhibitors and are thus useful as antihypercholesterolemic agents. In formula I and throughout this specification, the above symbols are defined as follows:

Z is

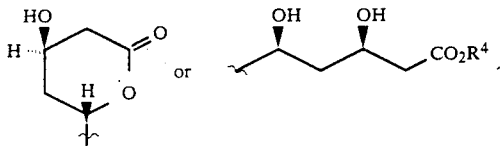

X is lower alkyl or lower alkenyl;
$R^1$ is aryl or alkyl;
$R^2$ and $R^3$ are the same or different and are hydrogen, lower alkyl, or aryl, or $R^2$ and $R^3$ taken together form a cycloalkyl group; and
$R^4$ is hydrogen, lower alkyl, alkali metal (such as sodium, lithium, or potassium) or a radical such as ammonium.

The terms "alkyl" and "alkoxy" include both straight and branched chain radicals of up to carbons, preferably 1 to 8 carbons. Exemplary alkyl groups are methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like. The terms "substituted alkyl" and "substituted alkoxy" refer to such groups having a halo-substituent, such as F, Br, Cl or I, a $CF_3$ substituent, an alkoxy substituent, an aryl substituent, an alkyl-aryl substituent, a haloaryl substituent, a cycloalkyl substituent or an alkylcycloalkyl substituent.

The term "alkenyl" by itself or as part of another group refers to both straight and branched chain groups. Those groups having 2 to 10 carbon atoms are preferred. The term "substituted alkenyl" refers to groups having one or two halo substituents, an alkoxy substituent, an aryl substituent, an alkyl-aryl substituent, a haloaryl substituent, a cycloalkyl substituent, or an alkylcycloalkyl substituent.

The terms "lower alkyl" and "lower alkenyl" refer to groups having 1 to 4 carbon atoms.

The term "cycloalkyl" includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl. The term "substituted cycloalkyl" refers to cycloalkyl groups substituted with 1 or 2 halogens, 1 or 2 lower alkyl groups and/or 1 or 2 lower alkoxy groups.

The term "aryl" or "Ar" as employed herein refers to monocyclic or bicyclic aromatic groups containing from 6 to 10 carbons in the ring portion, such as phenyl, and naphthyl. The term "substituted aryl" refers to substituted phenyl or substituted naphthyl, wherein the substituent on either the phenyl or naphthyl may be 1 or 2 lower alkyl groups, 1 or 2 halogens (Cl, Br or F), and/or 1 or 2 lower alkoxy groups.

The term "halogen" or "halo" refers to fluorine, chlorine, bromine and iodine.

Preferred compounds of formula I are those wherein:

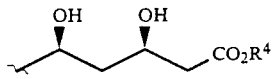

and $R^4$ is hydrogen, methyl, or lithium;
X is CH=CH—
$R^1$ is phenyl; and
one of $R^2$ and $R^3$ is methyl and the other is hydrogen.

The compounds of formula I of the invention will be formulated with a pharmaceutical vehicle or diluent. The pharmaceutical composition can be formulated in a classical manner with solid or liquid vehicles or diluents and pharmaceutical additives appropriate to the desired mode of administration. The compounds can be administered by an oral route (e.g., tablets, capsules, granules or powders) or a parenteral route (e.g., injectable preparations).

A typical capsule for oral administration contains active ingredients (25 mg), lactose (75 mg) and magnesium stearate (15 mg). The mixture is passed through a 60-mesh sieve and packed into a No. 1 gelatin capsule.

A typical injectable preparation is produced by asceptically placing 25 mg of a water-soluble salt of sterile active ingredient into a vial, asceptically freeze-drying and sealing. For use, the contents of the vial are mixed with 2 ml of physiological saline, to produce an injectable preparation.

The compounds of the invention are inhibitors of 3-hydroxy-3-methylglutaryl coenzyme A (HMG-CoA) reductase and inhibit cholesterol biosynthesis. Such compounds are useful in treating atherosclerosis to inhibit progression of disease, in treating hyperlipidemia to inhibit development of atherosclerosis and in treating nephrotic hyperlipidemia. In addition, the compounds of the invention increase plasma high density lipoprotein cholesterol levels.

As HMG CoA reductase inhibitors, the compounds of the invention may also be useful in inhibiting formation of gallstones and in treating tumors.

The compounds of the invention may also be employed in combination with antihyperlipoproteinemic agents, such as probucol, and/or with one or more serum cholesterol lowering agents such as Lopid ®

(gemfibrozil), bile acid sequestrants such as cholestyramine, colestipol, DEAE-Sephadex® as well as clofibrate, nicotinic acid and its derivatives, neomycin, p-aminosalicyclic acid, lovastatin, pravastatin, visinolin (velostatin, symvastatin or sinvinolin) and the like, and/or one or more squalene synthetase inhibitors.

The above compounds to be employed in combination with the HMG CoA reductase inhibitor of the invention will be used in amounts as indicated in the Physicians' Desk Reference (PDR).

The dose to be administered depends on the unitary dose, the symptoms, and the age and the body weight of the patient. A dose for adults is preferably between 20 and 2,000 mg per day, which can be administered in a single dose or in the form of individual divided doses from 1-4 times per day.

The compounds of this invention also have useful antifungal activities. For example, they may be used to control strains of *Penicillium sp., Aspergillus niger, Cladosporium sp., Cochliobolus miyabeorus* and *Helminthosporium cynodnotis*. For those utilities they are admixed with suitable formulating agents, powders, emulsifying agents or solvents (such as aqueous ethanol) and sprayed or dusted on the plants to be protected.

In addition, the compounds of the invention may also be useful in elevating HDL-cholesterol levels while lowering levels of LDL-cholesterol and serum triglycerides.

Compounds of formula I can be prepared by the following exemplary process.

A compound of the formula

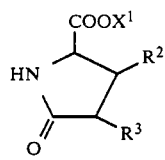

II wherein $X^1$ is lower alkyl, may be prepared as a mixture of diastereomers by procedures in A. B. Mauger, J. Org. Chem. 46 (1981), 1032. Ester compound II may be treated with a reducing agent (e.g., lithium aluminum hydride) in an inert solvent (e.g., tetrahydrofuran) under an inert atmosphere (e.g., nitrogen) at about 0° C. to obtain an alcohol of the formula

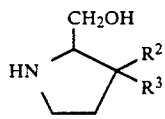

III as a mixture of cis and trans stereoisomers when $R^2$ and $R^3$ are not the same group.

Alcohol III may be reacted with an aroyl halide (e.g., benzoyl chloride) in a molar ratio of about 1:2 to 1:3 alcohol:halide in an organic solvent (e.g., tetrahydrofuran, pyridine) at about 0° to 30° C. to obtain a novel alcohol intermediate

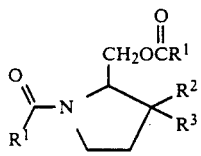

IV

Intermediate IV is reacted with an inorganic base like sodium hydroxide or sodium methoxide to obtain a novel alcohol intermediate

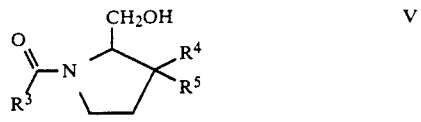

V as a mixture of cis and trans isomers where $R^4$ and $R^5$ are not the same group.

The cis and trans isomers of compound V may be separated by flash chromatography (see Example 1, compounds 1-F and 1-G) and oxidized with, for example, t-butanol and Dess-Martin periodinane in an organic solvent (e.g., dichloromethane) under an inert atmosphere (e.g., nitrogen) at about 20° to 30° C. to obtain a novel aldehyde intermediate

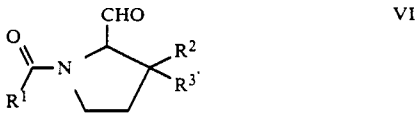

VI

The aldehyde VI may then be subjected to a Wittig-type coupling by treating it in an inert organic solvent such as acetonitrile or dimethylformamide (DMF) with a chiral β-keto-phosphonate

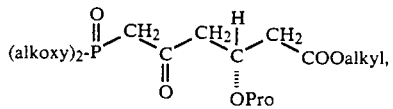

VII wherein Pro is a protecting group such as t-butyldimethylsilyl, at about 20° to 30° C. in the presence of a salt such as lithium chloride or magnesium chloride and an amine base such as 1,8-diazobicyclo [5.4.0]undec-7-ene (DBU), or isopropyldiethylamine to form a chiral olefinated novel intermediate

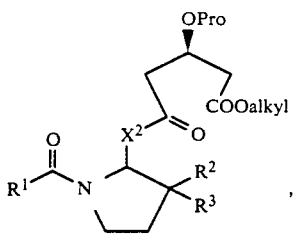

VIII wherein $X^z$ is alkenyl, as a mixture of chromatographically separable cis and trans isomers. The chiral keto-phosphonate VII is prepared as described in U.S. Pat. No. 4,804,770 and is employed in a molar ratio to aldehyde VI of about 1:1 to 2:1.

Olefin VIII may be deprotected by treatment with a fluoride (e.g., aqueous hydrofluoric acid in the presence of acetonitrile or tetrabutylammonium fluoride in the presence of acetic acid) at about 0° C. to form a novel ketol intermediate

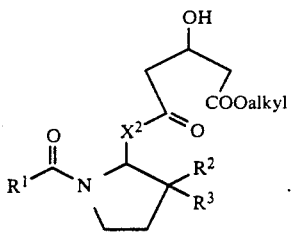

Compound I may be obtained by reducing the keto portion of ketol IX with a reducing agent (e.g., sodium borohydride) in the presence of triethylborane and pivalic acid in an inert organic solvent (e.g., tetrahydrofuran), thus forming the 1,3-diol compound I wherein X is $X^2$ (lower alkenyl), Z is the open-chain diol

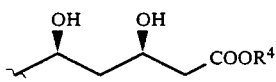

and $R^4$ is lower alkyl. The $R^4$ of this compound can be converted to alkali metal or ammonium by hydrolysis with an aqueous alkali metal or ammonium base (e.g., lithium hydroxide, sodium hydroxide) in an organic solvent (e.g., tetrahydrofuran, dioxane, acetonitrile). The $R^4$ can then be converted to hydrogen by treatment with a mild aqueous acid (e.g., potassium bisulfate). This open-chain acid can be lactonized by, for example, heating in toluene to about 100° to 130° C. or by treatment with a catalytic amount of trifluoroacetic acid at about ambient temperature in an organic solvent (e.g., ethyl acetate) to form compound I wherein Z is the lactone

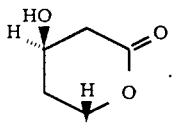

To form compounds of formula I wherein X is lower alkyl, the associated compound wherein X is lower alkenyl is hydrogenated in the presence of a catalyst (e.g., palladium on carbon) in an organic solvent (e.g., ethyl acetate).

The invention will now be further described by the following working examples, which are illustrative rather than limiting. In these examples, preparation of each intermediate compound appears just below the name of that intermediate. As a shorthand reference, the compound prepared in part 1-A will be referred to as "compound 1-A" or "intermediate 1-A"; likewise for compounds prepared in parts 1-B, 1-C, etc. All temperatures are in degrees Celsius (°C.). The term "Ce-Mo-$H_2SO_4$-heat" in all examples for thin layer chromatography (TLC) analysis refers to ceric sulfate, ammonium molybdate and sulfuric acid with heat for visualization.

EXAMPLE 1

(3R,5S,6E,cis)-7-(1-Benzoyl-3-methyl-2-pyrrolidin-yl)-3,5-dihydroxy-6-heptenoic acid, methyl ester

1-A. 5,5-Dicarbethoxy-4-methyl-2-pyrrolidinone

Sodium (400 mg, 17.4 mmol) was dissolved in absolute ethanol (100 ml) freshly distilled from magnesium turnings. Diethyl acetamidomalonate (21.7 g, 100 mmol, Aldrich Chem. Co.) was added under stirring, followed by ethyl crotonate (17.1 g, 150 mmol) over 5.0 minutes at ambient temperature under nitrogen atmosphere. After 15 minutes, the mixture was refluxed for 20 hours. It was then neutralized by acetic acid to pH of about 7.0, and the ethanol was evaporated in vacuo. The residue was then steam-distilled for 1.0 hour to remove the volatile materials and the distillate was discarded. The pot residue was saturated with salt and was extracted with ethyl acetate (3×120 mL). The extracts were combined, dried (anhydrous magnesium sulfate) and evaporated in vacuo to leave a solid residue (22 g). This material was crystallized once from ethyl acetatehexane to afford the title compound 1-A as colorless needles (15.5 g, 70%).

Melting point 75°–77° (according to Cocolas, et al., J. Amer. Chem. Soc. 79 (1957), 5203, melting point 76°–78° from water, yield=88%). The $^1$H and $^{13}$C-NMR spectra were consistent with the structure.

The reaction was subsequently repeated on 1½ scale to afford 26.5 g more of material. The yield in this preparation was 73%.

1-B. cis-5-Carbethoxy-4-methyl-2-pyrrolidinone and
1-C. trans-5-Carbethoxy-4-methyl-2-pyrrolidinone To a solution of compound 1-A (36.45 g, 150 mmol) in ethanol (150 mL) was added 1.0N sodium hydroxide (150 mL). After 24 hours, 1.0N hydrochloric acid was added and the solution was evaporated. The residue was treated with warm ethanol (175 mL) and filtered to remove sodium chloride. After evaporation, the residue was heated in an oil bath at 150° for 30 minutes, cooled, dissolved in ether (100 mL) filtered and evaporated. The residue was then distilled at boiling point 125°–135° and about 0.5 mm to afford a mixture (24.3 g, 95%) of compounds 1-B and 1-C as a colorless oil. According to Mauger, J. Org. Chem. 46 (1981), 1032, this oil was a 1:1 mixture of compounds 1-B and 1-C, which are difficult to separate by column chromatography on silica gel. Three successive crystallizations respectively from 140 mL, 70 mL and 140 mL of ether at -15° to −20°, with $^1$H and $^{13}$C-NMR monitoring, gave the homogeneous specimen of compound 1-B as prisms (6.2 g, 25.5%).

Melting point 58°–60° (according to Mauger, J. Org. Chem. 46 (1981), 1032, melting point 77.5° to −78° C., needles from ether).

This specimen of compound 1-B was homogeneous from its $^1$H and $^{13}$C-NMR spectra. Three attempted crystallizations of the material in the mother liquor from ether gave only a mixture of compound 1-B and 1-C.

1-D. cis-2-Hydroxymethyl-3-methylpyrrolidine and
1-E. trans-2-Hydroxymethyl-3-methylpyrrolidine A solution of the mixture containing about 25% of compound 1-B and 75% of compound 1-C (3.82 g, 22.3 mmol) in dry tetrahydrofuran (25 mL) was added dropwise under stirring into a chilled (ice-water bath) suspension of lithium aluminum hydride (30 mmol, 1.14 g) in dry tetrahydrofuran (30 mL) under nitrogen. After completion of the addition, the mixture was refluxed under stirring in an oil bath for 3½ hours. It was then cooled in an ice-bath, and 20% sodium hydroxide in water (28 mL) was added dropwise. After warming to ambient temperature, crushed solid sodium hydroxide (15 g) was added and the mixture was stirred for 45 minutes. The supernatant organic layer was separated by decantation and the aqueous layer was stirred vigorously with tetrahydrofuran, decanting the organic layer subsequently. This process was repeated three more times. The tetrahydrofuran solutions were then combined, dried (anhydrous magnesium sulfate) and evaporated in vacuo (at about 30°) to afford a mixture of compounds 1-D and 1-E as an oil (91.6 g, 63%). A thin layer chromatography examination showed the absence of the starting materials 1-B and 1-C. This material was used in the next step without further characterization.

1-F.
cis-1-Benzoyl-2-hydroxymethyl-3-methylpyrrolidine
and

1-G. trans-1-Benzoyl-2-hydroxymethyl-3-methyl pyrrolidine

A solution of the mixture of compounds 1-D and 1-E (1.6 g, 14.05 mmol) in dry tetrahydrofuran (25 mL) containing dry pyridine (3.16 g, 40 mmol) was cooled and stirred in an ice bath and benzoyl chloride (4.91 g, 35 mmol) was added in the course of 5.0 minutes. The mixture was then stirred at ambient temperature for 1.0 hour. Water (5.0 mL) was added and the stirring was continued for 20 minutes. The mixture was then added into 10% hydrochloric acid (50 mL) and extracted with dichloromethane (3×40 mL). The extracts were combined, washed with brine and a dilute sodium hydrogen carbonate solution and brine, dried (anhydrous magnesium sulfate) and was evaporated to afford the crude product (5.0 g) as an oil. A thin layer chromatography examination on silica gel (ethyl acetate) showed that this was a mixture of dibenzoylated compound 1-F and 1-G contaminated with some benzoic anhydride.

A solution of the above crude material (5.0 g) in methanol (25 mL) was stirred with commercial sodium methoxide (970 mg, 18 mmol) for 14 hours. It was then concentrated in vacuo, diluted with brine (30 mL) and extracted with dichloromethane (3×40 mL). The extracts were combined, washed with dilute brine (3×10 mL), dried (anhydrous magnesium sulfate) and evaporated to afford the crude product. A thin layer chromatography examination (silica gel, ethyl acetate) showed that this was a mixture of compound 1-F (more polar), compound 1-G and a small amount of methyl benzoate. This mixture was subjected to flash chromatography on LPS-1 silica gel using ethyl acetate-hexane (8:2) for elution to isolate compound 1-F (1.06 g, 34.5%) and compound 1-G (2.57 g, 51%) as homogeneous (thin layer chromatography) oils with consistent $^1$H and $^{13}$C-NMR data.

1-H. cis-1-Benzoyl-2-formyl-3-methylpyrrolidine

To a solution of compound 1-F (110 mg, 0.5 mmol) in dry dichloromethane (3.0 mL) containing t-butanol (44.5 mg, 0.6 mmol) under nitrogen was added Dess-Martin Periodinane (256 mg, 0.6 mmol, Aldrich Chemical Co.). This mixture was stirred at room temperature for 2.0 hours. It was then diluted with dichloromethane (5.0 mL) and stirred with a mixture of sodium hydrogen carbonate (453 mg, 5.4 mmol) and a 0.5N sodium thiosulfate solution (7.5 mL) until the dichloromethane solution was clear (about 30 minutes). The organic layer was then separated, washed with dilute brine, dried (anhydrous magnesium sulfate) and evaporated to afford the homogeneous compound 1-H (thin layer chromatography, silica gel, ethyl acetate) as an oil (1.05 mg, 96.4%) with consistent $^1$H and $^{13}$C-NMR spectral data. Repetition of the reaction on 1.16 (5.3 mmol) of compound 1-G gave 1.15 g of compound 1-H. Aldehyde 1-H was stored at −78° until use.

1-I.
(R)-6-(Dimethoxyphosphinyl)-3-[[(1,1-dimethylethyl)-dimethylsilyl]oxy]-5-oxo-hexanoic acid, methyl ester Compound 1-I was prepared as described in U.S. Pat. No. 4,804,770.

1-J.
(3R,6E,cis)-7-(1-Benzoyl-3-methyl-2-pyrrolidinyl)-3-[[(1,1-dimethylethyl)dimethyl]silyl]-oxy-5-oxo-6-heptenoic acid, methyl ester A mixture of aldehyde compound 1-H (1.09 g, 5.0 mmol), chiral phosphonate compound 1-I (2.10 g, 5.5 mmol) and lithium chloride (252 mg, 6.0 mmol) in dry acetonitrile (15 mL) was stirred at ambient temperature under an atmosphere of nitrogen. A solution of 1,8-diazabicyco (5,4,0) undec-7-ene (790 mg, 5.2 mmol) in acetonitrile (3.0 mL) was added. After 2½ hours, the mixture was poured into a 5% potassium bisulfate solution (100 ml) and extracted with ethyl acetate (3×40 mL). The extracts were combined, washed once with a 5% potassium bisulfate solution and brine, dried (anhydrous magnesium sulfate) and evaporated to afford the crude product as an oil. A thin layer chromatography examination (silica gel, ethyl acetate-hexane, 7:3) showed the absence of the starting aldehyde and the presence of essentially two partially separated less polar u.v. visible spots due to the two chiral diastereomers of compound 1-D. This was subjected to a flash chromatography on LPS-1 silica gel using ethyl acetatehexane (1:1) for elution to isolate compound 1-J as an oil (1.61 g, 61.5%) which was homogeneous by thin layer chromatography [$R_f$=0.4; silica gel, ethyl acetate-hexane (2:1), U.V.- and iodine visualization]. The $^1$H and $^{13}$C-NMR spectra were consistent with the structure and showed that it was a mixture of two diastereomers in the approximate ratio 45:55. Additionally, thin layer chromatography comparison with the corresponding product prepared from the trans-aldehyde (see Example 4) showed that none of the latter was present in this sample.

1-K.
(3R,6E,cis)-7-(1-Benzoyl-3-methyl-2-pyrrolidinyl)-3-hydroxy-5-oxo-6-heptenoic acid, methyl ester A solution of compound 1-J (344 mg, 0.727 mmol) in acetonitrile (4.0 mL) was stirred in an ice bath with 48% aqueous hydrofluoric acid (0.6 mL) for 1.0 hour. The mixture was then diluted with brine (20 mL) and extracted with methylene chloride (3×20 mL). The extracts were combined, washed with a dilute sodium hydrogen carbonate solution and brine, dried (anhydrous magnesium sulfate) and evaporated to afford the crude product as an oil. This crude product was purified by column chromatography on Baker 60-200 silica gel (15 g), eluting with methylene chloride, methylene chloride-ethyl acetate (8:2) and ethyl acetate to isolate compound 1-K as a thin layer chromatography-homogeneous oil ($R_f$=0.5, silica gel, ethyl acetate; u.v. and iodine visualization; 35 mg, 89.7%). On the basis of $^1$H and $^{13}$C-NMR data compound 1-K was a mixture of two diastereomers (about 45:55%) which were not readily separable by silica gel chromatography.

1-L.
(3R,5S,6E,cis)-7-(1-Benzoyl-3-methyl-2-pyrrolidinyl)-3,5-dihydroxy-6-heptenoic acid, methyl ester A solution of compound 1-K (234 mg, 0.65 mmol) in dry tetrahydrofuran (1.0 mL) containing a 1.0M solution of triethyl borane in tetrahydrofuran (0.96 mL) and pivalic acid (5.0 mg) was stirred under nitrogen atmosphere at ambient temperature for 20 minutes. It was then cooled to −78° in a dry ice-acetone bath and sodium borohydride (30.5 mg, 0.8 mmol) was added, followed dropwise by methanol in the course of 30 minutes. After 1.0 hour, a solution of 30% hydrogen peroxide (1.05 mL) in water (2.0 mL) was cautiously added. The mixture was warmed to ambient temperature and stirred for 30 minutes. The mixture was then adjusted to about pH 4.0 with 10% aqueous hydrochloric acid, diluted with brine (15 mL) and extracted with ethyl acetate (3×15 mL). The extracts were combined, washed with dilute sodium hydrogen carbonate and brine, dried (anhydrous magnesium sulfate) and evaporated to afford the crude product as a gum (232 mg). This product was subjected to column chromatography on Baker 60-200 silica gel (10 g), eluting the column with methylene chloride, methylene chloride-ethyl acetate (1:1), and ethyl acetate-methanol (98:2) to isolate Example 1 as a thin layer chromatographyhomogeneous oil ($R_f$=0.38, silica gel, ethyl acetate-methanol (95:5); u.v. and Ce-MO-$H_2SO_4$-heat visualization; 200 mg, 85%). The $^1H$ and $^{13}C$-NMR spectra were consistent with the structure.

EXAMPLE 2
(3R,5S,6E,cis))-7-(1-Benzoyl-3-methyl-2-pyrrolidinyl)-3,5-dihydroxy-6-heptenoic acid, monolithium salt A solution of Example 1 (200 mg, 0.552 mmol) in tetrahydrofuran (2.0 mL) was stirred with 1.0N aqueous lithium hydroxide (0.6 mL) for 1.0 hour under nitrogen. This mixture was evaporated in vacuo, dissolved in distilled water (5.0 mL) and applied on a column packed with HP-20 resin (2½"×1¼" bed). The column was eluted successively with deionized water (300 mL) and methanol-water (3:7; 200 mL). The methanol-water eluate was concentrated in vacuo and lyophilized to afford the analytical specimen of Example 2 as a colorless fluffy solid (162 mg, 83.1%, $R_f$=0.27, 8:2:1 silica gel, ethyl acetate-hexane-acetic acid) with consistent IR and $^1H$-NMR spectra.

Analysis calculated for $C_{19}H_{24}LiNO_4$·0.95 $H_2O$ (MW=353.33/370.52):

C,61.59; H,7.05; N,3.78% Found: C,61.52; H,6.86; N,3.85%

IR Spectrum: $\mu$max 3405-3421 $Cm^{-1}$ (Strong, OH) 1576-1608 $Cm^{-1}$ (Strong, C=O) ~1425 $Cm^{-1}$ (Strong, C=O).

$^1$H-NMR Spectrum (DMSO-$d_6$, FX-270). δ0.83, 0.95 (doublet, J=7.0, CH$_3$ of two diastereomers) 4.05 (m, 2H, CHOH) 4.65, 4.18 (broad s, ~½H each, CH-N) 5.10, 5.42 (m, 1H each, CH=CH 7.41, 7.44 (s, 5H, aromatic H) ppm.

EXAMPLE 3
(3R,5S,6E,trans)-7-(1-Benzyl-3-methyl-2-pyrrolidinyl)-3,5-dihydroxy-6-heptenoic acid, monolithium salt 3-A. trans-1-Benzoyl-2-formyl-3-methylpyrrolidine A solution of compound 1-G (550 mg, 2.71 mmol) in dry dichloromethane (15 mL) was stirred with t-butanol (225 mg, 3.0 mmol) and Dess-Martin Periodinane (1.28 g, 3.0 mmol) under nitrogen atmosphere of nitrogen for 1.0 hour. It was then diluted with dichloromethane (15 mL) and stirred well with a mixture of sodium hydrogen carbonate (2.27 g) and 0.5N sodium thiosulfate (38 mL) for 30 minutes. The dichloromethane layer was then separated, washed with brine, dried (anhydrous magnesium sulfate) and evaporated to afford compound 3-A as a solid (548 mg, 100%), which was essentially homogeneous by thin layer chromatography (silica gel, ethyl acetate) and showed $^1H$ and $^{13}C$-NMR spectra consistent with the structure. A specimen crystallized from ethyl acetate-hexane at about −20° C. showed melting point 83°-84° C. Characteristically, in the $^1H$-NMR spectrum in CDCl$_3$, the CH$_3$, CH—CHO and CHO protons resonated respectively at 1.23, 4.05 and 9.6 ppm.

3-B.
(3R,6E,trans)-7-(1-Benzoyl-3-methyl-2-pyrrolidinyl)-3-[[(1,1-dimethylethyl)-dimethyl]silyl]-oxy-5-oxo-6-heptenoic acid, methyl ester A mixture of compound 3-A (525 mg, 2.42 mmol), compound 1-I (970 mg, 2.54 mmol) and lithium chloride (103 mg, 2.42 mmol) was stirred in dry acetonitrile (8.0 mL) under nitrogen and a solution of 1,8-diazabicyclo (5,4,0) undec-7-ene (350 mg, 2.3 mmol) was added. After 2.0 hours, the mixture was added into 5% aqueous potassium bisulfate (50 mL) and extracted with methylene chloride (3×30 mL). The extracts were combined, washed once with a 5% aqueous potassium bicarbonate solution and brine, dried (anhydrous magnesium sulfate) and evaporated to afford the crude product as an oil. A thin layer chromatography examination of this oil (silica gel, ethyl acetate) did not show the presence of any starting aldehyde. It was subjected to flash chromatography on LPS-1 silica gel, eluting the column with ethyl acetate-hexane (1:1) to isolate compound 3-A as a homogeneous [$R_f$=0.35; silica gel, ethyl acetate-hexane (1:1); U.V.; Ce-Mo-$H_2SO_4$-heat] oil (756 mg, 66.3) with consistent $^1H$ and $^{13}C$-NMR spectral data.

3-C.
(3R,6E,trans)-7-1-Benzoyl-3-methyl-2-pyrrolidinyl)-3-hydroxy-5-oxo-6-heptenoic acid, methyl ester A solution of compound 3-B (473 mg, 1.0 mmol) in acetonitrile (3.5 mL) was stirred at ambient temperature with 48% hydrofluoric acid (0.3 mL) for 1½ hours. It was then added into brine (25 mL) and extracted with dichloromethane (3×20 mL). The extracts were combined, washed with a diluted sodium hydrogen carbonate solution and brine, dried (anhydrous magnesium sulfate) and was evaporated to afford the crude product as an oil. This was chromatographed on a column of Baker 60-200 silica gel (5 g, eluting with methylene chloride, 7:3 methylene chloride-ethyl acetate and ethyl acetate) to afford homogeneous (thin layer chromatography, silica gel, ethyl acetate) compound 3-C as an oil (300 mg, 83%) with consistent $^1H$ and $^{13}C$-NMR spectral data.

3-D.
(3R,5S,6E,trans)-7-(1-Benzoyl-3-methyl-2-pyrrolidinyl)-3,5-dihydroxy-6-heptenoic acid, methyl ester A solution of compound 3-C (248 mg, 0.685 mmol) in dry tetrahydrofuran (2.0 mL) was mixed with 1.0M triethyl borane in tetrahydrofuran (1.03 mL) and pivalic acid (5.0 mg) and stirred under nitrogen at ambient temperature for 25 minutes. The mixture was then cooled at −78° in a dry ice-acetone bath, and sodium borohydride (32.7 mg, 0.86 mmol) was added followed dropwise by dry methanol (0.9 mL). After 1.0 hour, a solution of 30% hydrogen peroxide (1.5 mL) in water (1.5 mL) was cautiously added, the mixture was warmed to ambient temperature and stirred for 30 minutes. The mixture was then adjusted to about pH 4.0 with dilute hydrochloric acid, diluted with brine (20 mL) and extracted with ethyl acetate (3×15 mL). The extracts were combined, washed with brine, dried and evaporated in vacuo. The residue was chromatographed on a column of silica gel (Baker 60–200 mesh, 10 g), eluting the column with methylene chloride, methylene chloride-ethyl acetate (1:1), ethyl acetate and ethyl acetatemethanol (95:5) to isolate homogeneous (thin layer chromatography; silica gel, 9:1 ethyl acetatemethanol) Example 3 as an oil (229 mg, 92%) with consistent $^1$H and $^{13}$C-NMR spectral data.

EXAMPLE 4

(3R,5S,6E,trans)-7-(1-Benzoyl-3-methyl-2-pyrrolidinyl)-3,5-dihydroxy-6-heptenoic acid, monolithium salt A solution of Example 3 (180 mg, 0.495 mmol) in tetrahydrofuran (2.5 mL) was stirred under nitrogen with 1N aqueous lithium hydroxide (0.5 mL) for 30 minutes. The mixture was then concentrated in vacuo, dissolved in distilled water (4.0 mL) and applied on an HP-20 polymer column (3"×1¼"). The column was eluted with deionized water (200 mL), followed by methanol-water (3:7; 200 mL). The methanol-water eluate was concentrated in vacuo and lyophilized to afford the analytical specimen of Example 4 as a colorless fluffy solid (147 mg, 85%), R$_f$=0.29 (silica gel, 8:2:1 ethyl acetate-hexane-acetic acid) with consistent IR and $^1$H-NMR spectral data.

Analysis calculated for C$_{19}$H$_{24}$LiNO$_5$·0.76 H$_2$O (MW=367.10): C,62.16; H,7.01: N,3.82% Found: C,62.43; H,7.20; N,3.77%

IR Spectrum: μmax 3391–3423 Cm$^{-1}$ (Strong, OH) 1601, 1612 Cm$^{-1}$ (Strong, C=O) 1426 Cm$^{-1}$ (Strong, C=O)

$^1$H-NMR Spectrum: (DMSO-d$_6$, FX-270) δ1.0(d,3H,J=~8.0,CH$_3$) ~3.5 (broad,NCH) ~3.5–4.2 (broad, CH—OH and CH—OH) 5.05,5.30 (broad,1H,C=CH) 5.55 (broad,1H,C=CH) ~7.40 (m,5H,aromatic protons)ppm.

What is claimed is:

1. A compound of the formula

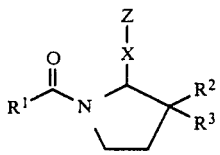

wherein:
Z is

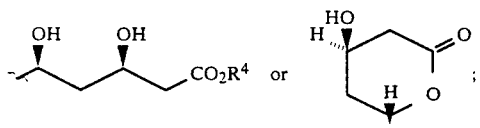

X is —(CH$_2$)$_n$— or —(CH$_2$)$_p$—CH=CH—(CH$_2$)$_q$—;

n is 1, 2, 3 or 4;
p and q are each independently 0, 1, or 2, provided that p+q=2;
R$^1$ is aryl, substituted aryl, alkyl or substituted alkyl;
R$^2$ and R$^3$ are the same or different and are hydrogen, lower alkyl, lower substituted alkyl, aryl or substituted aryl; or R$^2$ and R$^3$ taken together form a cycloalkyl or substituted cycloalkyl group; and
R$^4$ is hydrogen, lower alkyl, substituted lower alkyl, alkali metal, or ammonium;
and wherein:
"alkyl" and "alkoxy" refer to straight and branched chain radicals of up to 12 carbons;
"lower alkyl" refers to groups having 1 to 4 carbons;
"substituted alkyl" and "substituted alkoxy" refer to groups having a halo, —CF$_3$, alkoxy, aryl, alkylaryl, haloaryl, cycloalkyl, or alkylcycloalkyl substituent;
"cycloalkyl" refers to saturated, cyclic hydrocarbon groups having 3 to 12 carbons;
"substituted cycloalkyl" refers to cycloalkyl groups substituted with 1 or 2 halogens, 1 or 2 lower alkyl and/or 1 or 2 lower alkoxy groups;
"aryl" refers to monocyclic or bicyclic aromatic groups having 6 to 10 carbons in the ring;
"substituted aryl" refers to aryl groups having 1 or 2 lower alkyl, 1 or 2 lower alkoxy, and/or 1 or 2 halogen substituents; and
"halogen" and "halo" refer to Cl, Br, I and F.

2. The compound of claim 1, wherein:
Z is

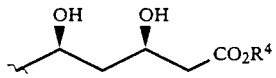

and R$^4$ is hydrogen, methyl, or lithium.

3. The compound of claim 1, wherein R$^1$ is phenyl.
4. The compound of claim 1, wherein one of R$^2$ and R$^3$ is methyl and the other is hydrogen.
5. The compound of claim 1, wherein X is —CH=CH—.
6. The compounds of claim 1, having the names:
(3R,5S,6E,cis)-7-(1-Benzoyl-3-methyl-2-pyrrolidinyl)-3,5-dihydroxy-6-heptenoic acid, methyl ester;
(3R,5S,6E,cis))-7-(1-Benzoyl-3-methyl-2-pyrrolidinyl)-3,5-dihydroxy-6-heptenoic acid, monolithium salt;
(3R,5S,6E,trans)-7-(1-Benzoyl-3-methyl-2-pyrrolidinyl)-3,5-dihydroxy-6-heptenoic acid, methyl ester;
(3R,5S,6E,trans)-7-(1-Benzoyl-3-methyl-2-pyrrolidinyl)-3,5-dihydroxy-6-heptenoic acid, monolithium salt.
7. A method of inhibiting or treating hypercholesterolemia which comprises administering to a patient in need of such treatment an effective amount of a compound as defined in claim 1.
8. A method of inhibiting or treating atherosclerosis, which comprises administering to a patient in need of such treatment an effective amount of a compound as defined in claim 1.
9. A hypocholesterolemic or hypolipemic composition comprising a compound as defined in claim 1 and a pharmaceutically acceptable carrier therefor.
10. A method of inhibiting cholesterol biosynthesis, which comprises administering to a patient in need of such treatment a cholesterol biosynthesis-inhibiting amount of a compound as defined in claim 1.

* * * * *